United States Patent
Himoto et al.

(10) Patent No.: US 12,302,683 B2
(45) Date of Patent: May 13, 2025

(54) DETECTION DEVICE

(71) Applicant: Japan Display Inc., Tokyo (JP)

(72) Inventors: Kento Himoto, Tokyo (JP); Takashi Nakamura, Tokyo (JP)

(73) Assignee: Japan Display Inc., Tokyo (JP)

( * ) Notice: Subject to any disclaimer, the term of this patent is extended or adjusted under 35 U.S.C. 154(b) by 346 days.

(21) Appl. No.: 17/890,642

(22) Filed: Aug. 18, 2022

(65) Prior Publication Data

US 2023/0054533 A1 Feb. 23, 2023

(30) Foreign Application Priority Data

Aug. 23, 2021 (JP) ................. 2021-135625

(51) Int. Cl.
| | | |
|---|---|---|
| *H10K 39/32* | (2023.01) | |
| *A61B 5/00* | (2006.01) | |
| *G06V 10/143* | (2022.01) | |
| *G06V 40/12* | (2022.01) | |

(Continued)

(52) U.S. Cl.
CPC .............. *H10K 39/32* (2023.02); *A61B 5/489* (2013.01); *G06V 10/143* (2022.01); *G06V 40/1318* (2022.01); *G06V 40/1341* (2022.01); *G06V 40/145* (2022.01)

(58) Field of Classification Search
CPC ........ H10K 39/32; H10K 39/34; H10K 39/38; H01L 27/14665; H01L 27/14667; H01L 27/14669; H01L 27/14678
See application file for complete search history.

(56) References Cited

U.S. PATENT DOCUMENTS

| | | | |
|---|---|---|---|
| 9,847,366 B1 * | 12/2017 | Kim ................... | G01J 1/4228 |
| 2008/0144268 A1 | 6/2008 | Konno et al. | |

(Continued)

FOREIGN PATENT DOCUMENTS

| | | |
|---|---|---|
| JP | 63-086474 | 4/1988 |
| JP | 2006093521 | 4/2006 |
| JP | 2007103578 | 4/2007 |

(Continued)

OTHER PUBLICATIONS

Japanese Office Action issued Oct. 8, 2024 in corresponding Japanese Application No. 2021-135625.

*Primary Examiner* — Zandra V Smith
*Assistant Examiner* — Molly K Reida
(74) *Attorney, Agent, or Firm* — K&L Gates LLP

(57) ABSTRACT

A detection device includes a substrate, a plurality of photodiodes provided on the substrate, a plurality of transistors provided correspondingly to the respective photodiodes, a plurality of gate lines that extend in a first direction, a plurality of signal lines that extend in a second direction intersecting the first direction, a plurality of lower electrodes that are provided between the transistors and the photodiodes in a direction orthogonal to the substrate, and are provided correspondingly to the respective photodiodes, an upper electrode provided so as to extend across the photodiodes, and a reflective layer provided between the substrate and each of the photodiodes in the direction orthogonal to the substrate. Each of the lower electrodes has a smaller area than an area defined by the gate lines and the signal lines, and the reflective layer is provided between the lower electrodes adjacent to each other in a plan view.

11 Claims, 15 Drawing Sheets

(51) Int. Cl.
　　　*G06V 40/13*　　　(2022.01)
　　　*G06V 40/145*　　(2022.01)

(56) References Cited

U.S. PATENT DOCUMENTS

2009/0027358 A1　1/2009　hosono
2022/0190038 A1　6/2022　Tada et al.

FOREIGN PATENT DOCUMENTS

| JP | 2008153361 | 7/2008 |
| JP | 2009032005 A | 2/2009 |
| JP | 201422557 | 12/2014 |
| WO | 2021/049262 | 8/2020 |

\* cited by examiner

DETECTION DEVICE

CROSS-REFERENCE TO RELATED APPLICATION

This application claims the benefit of priority from Japanese Patent Application No. 2021-135625 filed on Aug. 23, 2021, the entire contents of which are incorporated herein by reference.

BACKGROUND

1. Technical Field

The present disclosure relates to a detection device.

2. Description of the Related Art

Optical sensors capable of detecting fingerprint patterns and vein patterns are known (for example, Japanese Patent Application Laid-open Publication No. 2009-032005). Such optical sensors each include a plurality of photodiodes each including an organic semiconductor material used as an active layer. Each of the photodiodes is disposed between a lower electrode and an upper electrode.

A sensor capacity generated between the lower electrode and the upper electrode can be increased by thinning the active layer of the photodiode. The sensor capacity stores therein an electric charge generated when the photodiode is irradiated with light. Thinning the active layer of the photodiode, however, reduces the amount of light absorbable by the photodiode when the photodiode is irradiated with the light, which may reduce the light use efficiency.

It is an object of the present disclosure to provide a detection device capable of increasing the light use efficiency.

SUMMARY

A detection device according to an embodiment of the present disclosure includes a substrate, a plurality of photodiodes provided on the substrate, a plurality of transistors provided correspondingly to the respective photodiodes, a plurality of gate lines that extend in a first direction, a plurality of signal lines that extend in a second direction intersecting the first direction, a plurality of lower electrodes that are provided between the transistors and the photodiodes in a direction orthogonal to the substrate, and are provided correspondingly to the respective photodiodes, an upper electrode provided so as to extend across the photodiodes, and a reflective layer provided between the substrate and each of the photodiodes in the direction orthogonal to the substrate. Each of the lower electrodes has a smaller area than an area defined by the gate lines and the signal lines, and the reflective layer is provided between the lower electrodes adjacent to each other in a plan view.

DETAILED DESCRIPTION

Figure 1:
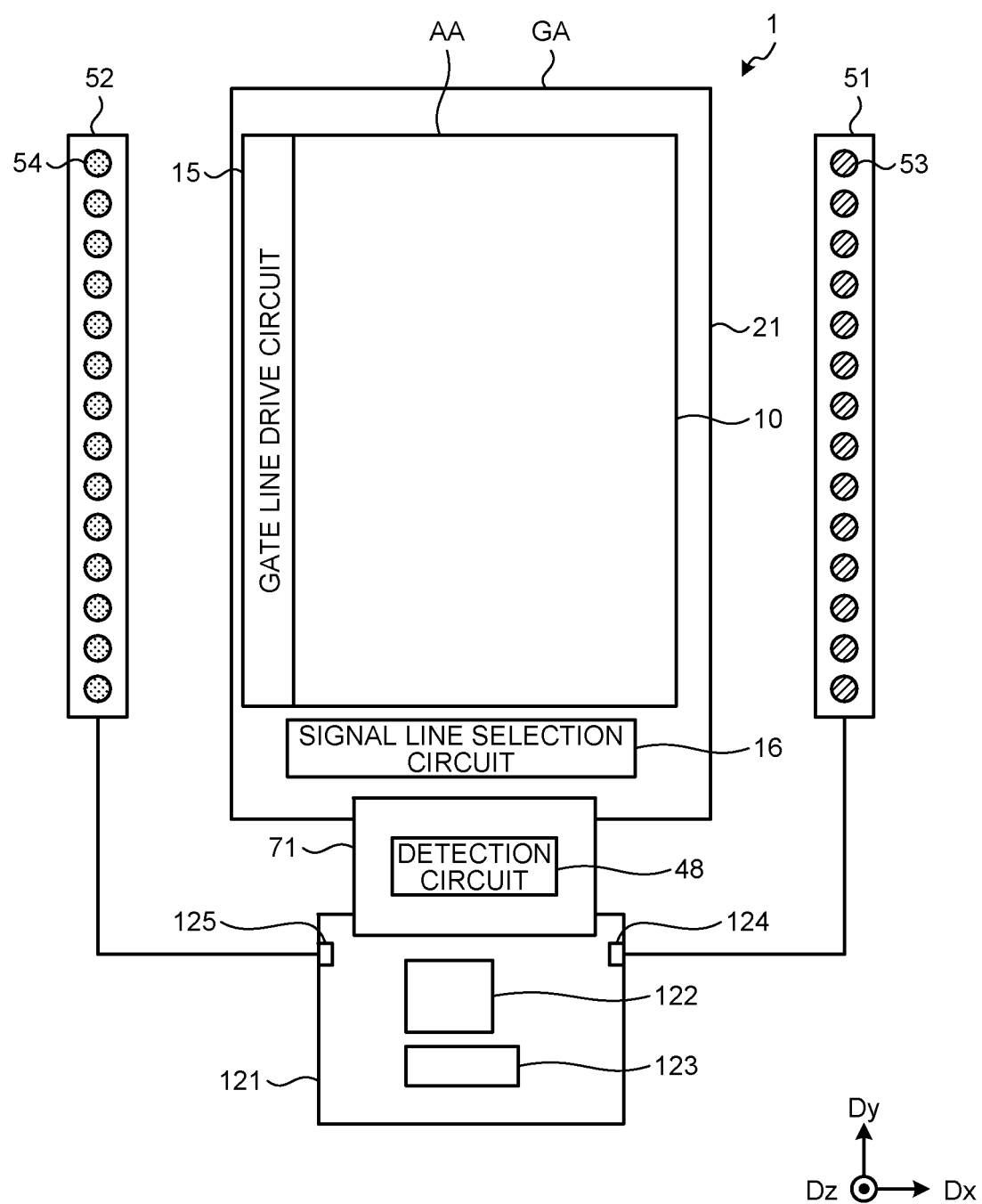
FIG. 1 is a plan view illustrating a detection device according to a first embodiment.

The following describes modes (embodiments) for carrying out the present disclosure in detail with reference to the drawings. The present disclosure is not limited to the description of the embodiments to be given below. Components to be described below include those easily conceivable by those skilled in the art or those substantially identical thereto. In addition, the components to be described below can be combined as appropriate. What is disclosed herein is merely an example, and the present disclosure naturally encompasses appropriate modifications easily conceivable by those skilled in the art while maintaining the gist of the present disclosure. To further clarify the description, the drawings may schematically illustrate, for example, widths, thicknesses, and shapes of various parts as compared with actual aspects thereof. However, they are merely examples, and interpretation of the present disclosure is not limited thereto. The same component as that described with reference to an already mentioned drawing is denoted by the same reference numeral through the present disclosure and the drawings, and detailed description thereof may not be repeated where appropriate.

In the present specification and claims, in expressing an aspect of disposing another structure above a certain structure, a case of simply expressing "above" includes both a case of disposing the other structure immediately above the certain structure so as to contact the certain structure and a case of disposing the other structure above the certain structure with still another structure interposed therebetween, unless otherwise specified.

First Embodiment

FIG. 1 is a plan view illustrating a detection device according to a first embodiment. As illustrated in FIG. 1, a detection device 1 includes a substrate 21, a sensor 10, a gate line drive circuit 15, a signal line selection circuit 16, a detection circuit 48, a control circuit 122, a power supply circuit 123, a first light source base material 51, a second light source base material 52, first light sources 53, and second light sources 54. The first light source base material 51 is provided with the first light sources 53. The second light source base material 52 is provided with the second light sources 54.

The substrate 21 is electrically coupled to a control board 121 through a wiring board 71. The wiring board 71 is, for example, a flexible printed circuit board or a rigid circuit board. The wiring board 71 is provided with the detection circuit 48. The control board 121 is provided with the control circuit 122 and the power supply circuit 123. The control circuit 122 is, for example, a field-programmable gate array (FPGA). The control circuit 122 supplies control signals to the sensor 10, the gate line drive circuit 15, and the signal line selection circuit 16 to control a detection operation of the sensor 10. The control circuit 122 supplies control signals to the first and the second light sources 53 and 54 to control lighting or non-lighting of the first and the second light sources 53 and 54. The power supply circuit 123 supplies voltage signals including, for example, a sensor power supply signal VDDSNS (refer to FIG. 5) to the sensor 10, the gate line drive circuit 15, and the signal line selection circuit 16. The power supply circuit 123 supplies a power supply voltage to the first and the second light sources 53 and 54.

The substrate 21 has a detection area AA and a peripheral area GA. The detection area AA is an area provided with a plurality of photodiodes PD (refer to FIG. 5) included in the sensor 10. The peripheral area GA is an area between the outer perimeter of the detection area AA and ends of the substrate 21, and is an area not provided with the photodiodes PD.

The gate line drive circuit 15 and the signal line selection circuit 16 are provided in the peripheral area GA. Specifically, the gate line drive circuit 15 is provided in an area extending along a second direction Dy in the peripheral area GA. The signal line selection circuit 16 is provided in an area extending along a first direction Dx in the peripheral area GA, and is provided between the sensor 10 and the detection circuit 48.

In the following description, the first direction Dx is one direction in a plane parallel to the substrate 21. The second direction Dy is one direction in the plane parallel to the substrate 21, and is a direction orthogonal to the first direction Dx. The second direction Dy may non-orthogonally intersect the first direction Dx. The term "plan view" refers to a positional relation when viewed from a direction orthogonal to the substrate 21.

The first light sources 53 are provided on the first light source base material 51, and are arranged along the second direction Dy. The second light sources 54 are provided on the second light source base material 52, and are arranged along the second direction Dy. The first light source base material 51 and the second light source base material 52 are electrically coupled, through terminals 124 and 125, respectively, provided on the control board 121, to the control circuit 122 and the power supply circuit 123.

For example, inorganic light-emitting diodes (LEDs) or organic electroluminescent (EL) diodes (organic light-emitting diodes (OLEDs)) are used as the first and the second light sources 53 and 54. The first and the second light sources 53 and 54 emit first and second light, respectively, having different wavelengths.

The first light emitted from the first light sources 53 is mainly reflected on a surface of an object Fg to be detected, such as a finger, and is incident on the sensor 10. As a result, the sensor 10 can detect a fingerprint by detecting a shape of asperities on the surface of the finger or the like. The second light emitted from the second light sources 54 is mainly reflected in the finger or the like, or transmitted through the finger or the like, and is incident on the sensor 10. As a result, the sensor 10 can detect information on a living body in the finger or the like. Examples of the information on the living body include a pulse wave, pulsation, and a vascular image of the finger or a palm. That is, the detection device 1 may be configured as a fingerprint detection device to detect the fingerprint or a vein detection device to detect a vascular pattern of, for example, veins.

The first light may have a wavelength of from 500 nm to 600 nm, for example, a wavelength of approximately 550 nm, and the second light may have a wavelength of from 780 nm to 950 nm, for example, a wavelength of approximately 850 nm. In this case, the first light is blue or green visible light, and the second light is infrared light. The sensor 10 can detect the fingerprint based on the first light emitted from the first light sources 53. The second light emitted from the second light sources 54 is reflected in the object Fg to be detected, such as the finger, or transmitted through or absorbed by the finger or the like, and is incident on the sensor 10. As a result, the sensor 10 can detect the pulse wave or the vascular image (vascular pattern) as the information on the living body in the finger or the like.

Alternatively, the first light may have a wavelength of from 600 nm to 700 nm, for example, approximately 660 nm, and the second light may have a wavelength of from 780 nm to 900 nm, for example, approximately 850 nm. In this case, the sensor 10 can detect a blood oxygen saturation level in addition to the pulse wave, the pulsation, and the vascular image as the information on the living body based on the first light emitted from the first light sources 53 and the second light emitted from the second light sources 54. Thus, the detection device 1 includes the first and the second light sources 53 and 54, and therefore, can detect the various information on the living body by performing the detection based on the first light and the detection based on the second light.

The arrangement of the first and the second light sources 53 and 54 illustrated in FIG. 1 is merely an example, and can be changed as appropriate. The detection device 1 is provided with a plurality of types of light sources (first and second light sources 53 and 54) as the light sources. However, the light sources are not limited thereto, and may be of one type. For example, the first and the second light sources 53 and 54 may be arranged on each of the first and the second light source base materials 51 and 52. The first and the second light sources 53 and 54 may be provided on one light source base material, or three or more light source base materials. Alternatively, only at least one light source needs to be disposed.

Figure 2:
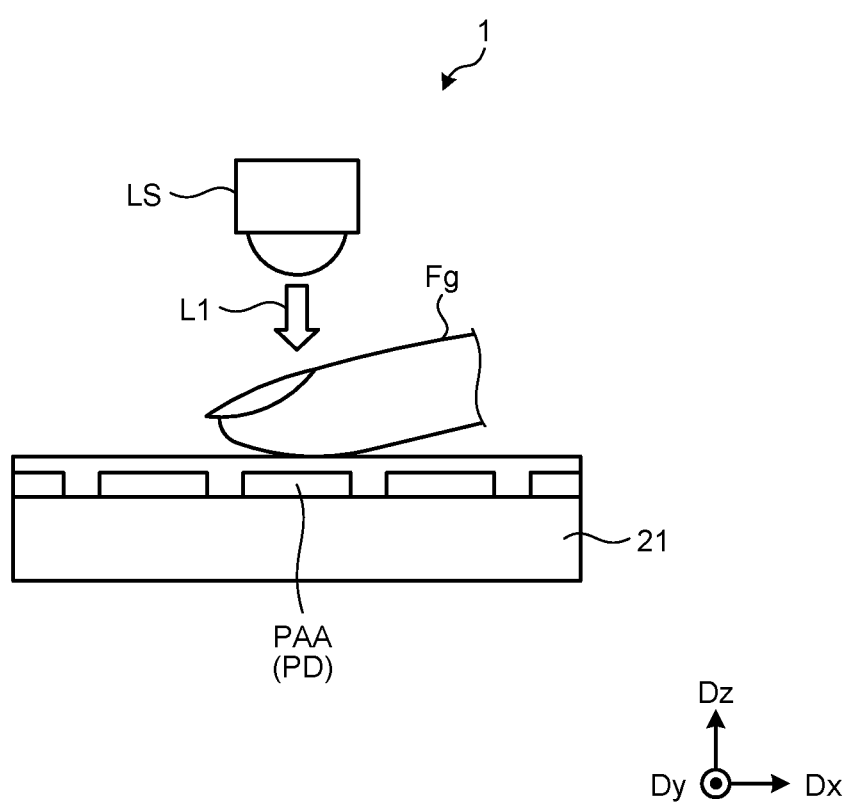
FIG. 2 is a sectional view illustrating a schematic sectional configuration of the detection device according to the first embodiment.

FIG. 2 is a sectional view illustrating a schematic sectional configuration of the detection device according to the first embodiment. As illustrated in FIG. 2, a plurality of detection elements PAA including the photodiodes PD are arranged above the substrate 21. Each of the photodiodes PD is an organic photodiode (OPD) using an organic semiconductor. A light source LS is provided above the substrate 21 and the photodiodes PD so as to have the object Fg to be detected, such as the finger, interposed between the light source LS and the photodiodes PD. Light L1 emitted from the light source LS passes through the object Fg to be detected, and irradiates the photodiodes PD. The photodiodes PD can detect information on the object Fg to be detected, using the light L1 emitted from the light source LS.

The detection device 1 illustrated in FIG. 2 is a transmissive detection device that detects the light L1 transmitted through the object Fg to be detected. However, the detection device 1 is not limited thereto, and may be a reflective detection device. The light source LS illustrated in FIG. 2 includes at least either of the first light sources 53 and the second light sources 54 described above. However, the number, arrangement, and the like of the light sources LS can be changed as appropriate.

Figure 3:
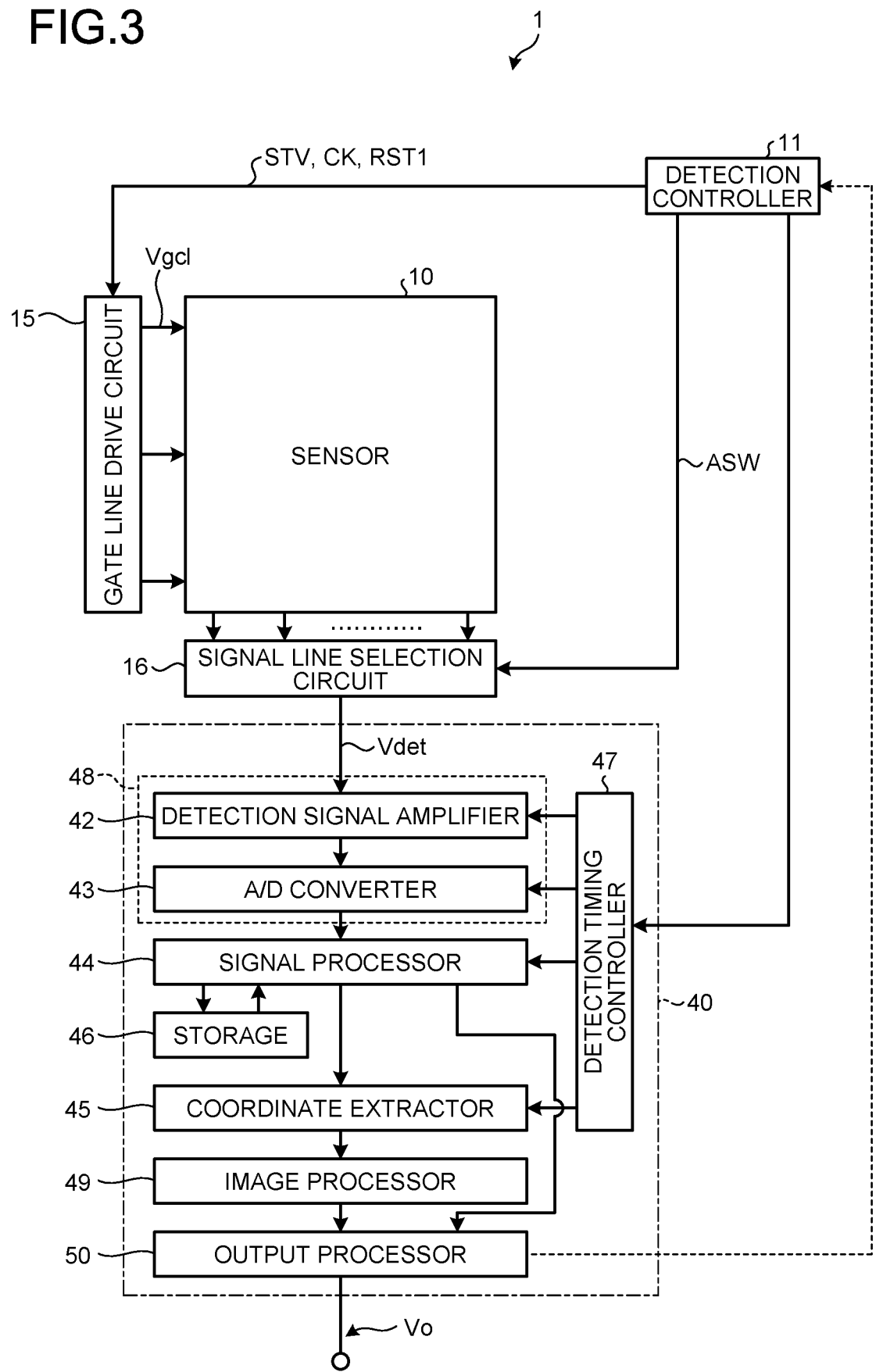
FIG. 3 is a block diagram illustrating a configuration example of the detection device according to the first embodiment.

FIG. 3 is a block diagram illustrating a configuration example of the detection device according to the first embodiment. As illustrated in FIG. 3, the detection device 1 further includes a detection controller 11 and a detector 40. The control circuit 122 includes one, some, or all functions of the detection controller 11. The control circuit 122 also includes one, some, or all functions of the detector 40 except those of the detection circuit 48.

The sensor 10 includes the photodiodes PD. Each of the photodiodes PD included in the sensor 10 outputs an electrical signal corresponding to light irradiating the photodiode PD as a detection signal Vdet to the signal line selection circuit 16. The sensor 10 perform the detection in response to a gate drive signal Vgcl supplied from the gate line drive circuit 15.

The detection controller 11 is a circuit that supplies respective control signals to the gate line drive circuit 15, the signal line selection circuit 16, and the detector 40 to control operations thereof. The detection controller 11 supplies various control signals such as a start signal STV, a clock signal CK, and a reset signal RST1 to the gate line drive circuit 15. The detection controller 11 also supplies various control signals such as a selection signal ASW to the signal line selection circuit 16. The detection controller 11 supplies various control signals to the first and the second light sources 53 and 54 to control the lighting and non-lighting of the respective first and second light sources 53 and 54.

The gate line drive circuit 15 is a circuit that drives a plurality of gate lines GCL (refer to FIG. 4) based on the various control signals. The gate line drive circuit 15 sequentially or simultaneously selects the gate lines GCL, and supplies the gate drive signals Vgcl to the selected gate lines GCL. Through this operation, the gate line drive circuit 15 selects the photodiodes PD coupled to the gate lines GCL.

Figure 4:
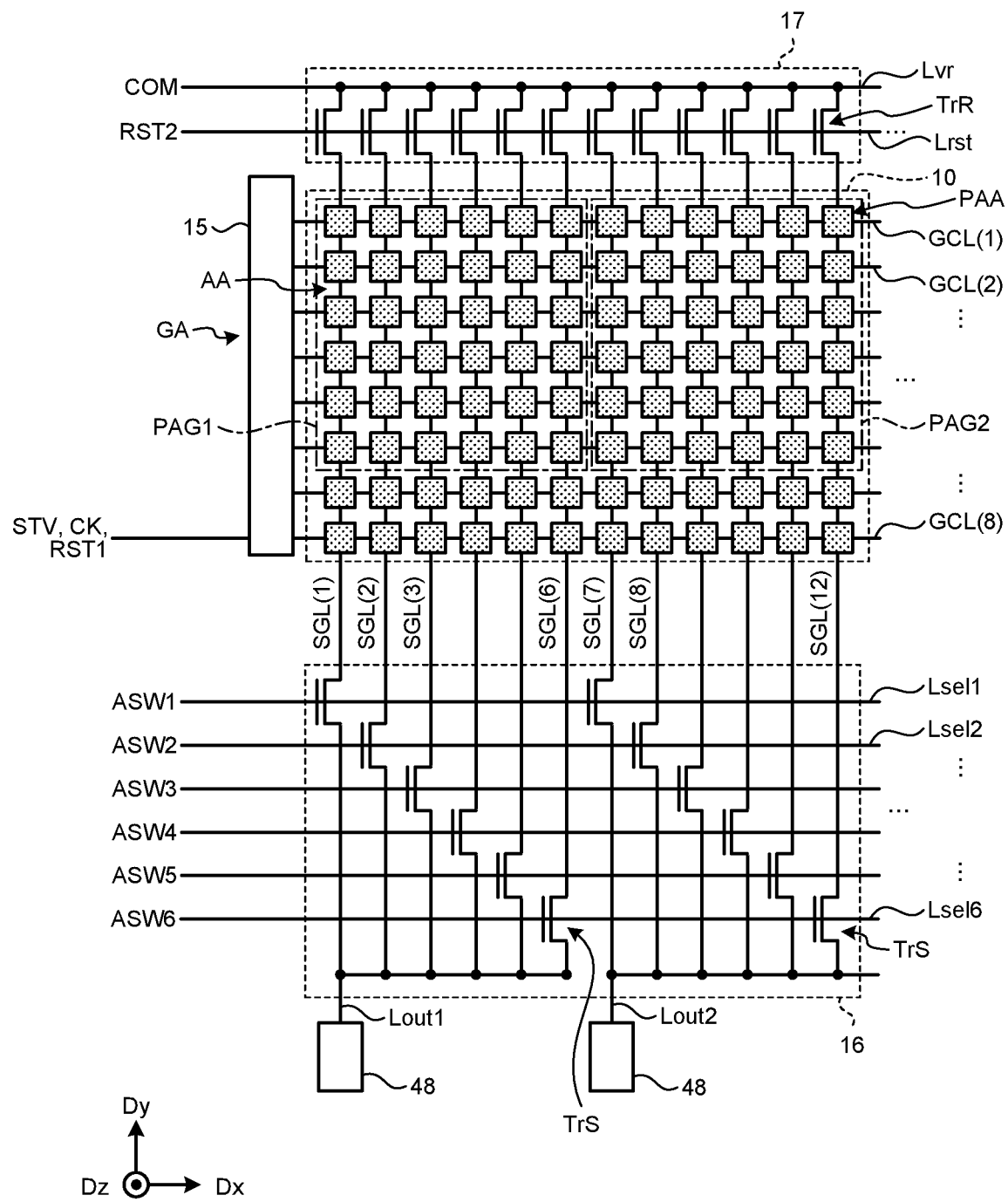
FIG. 4 is a circuit diagram illustrating the detection device.

The signal line selection circuit 16 is a switch circuit that sequentially or simultaneously selects a plurality of signal lines SGL (refer to FIG. 4). The signal line selection circuit 16 is, for example, a multiplexer. The signal line selection circuit 16 couples the selected signal lines SGL to the detection circuit 48 based on the selection signal ASW supplied from the detection controller 11. Through this operation, the signal line selection circuit 16 outputs the detection signals Vdet of the photodiodes PD to the detector 40.

The detector 40 includes the detection circuit 48, a signal processor 44, a coordinate extractor 45, a storage 46, a detection timing controller 47, an image processor 49, and an output processor 50. Based on a control signal supplied from the detection controller 11, the detection timing controller 47 controls the detection circuit 48, the signal processor 44, the coordinate extractor 45, and the image processor 49 so as to operate in synchronization with one another.

The detection circuit 48 is, for example, an analog front-end (AFE) circuit. The detection circuit 48 is a signal processing circuit having functions of at least a detection signal amplifier 42 and an analog-to-digital (A/D) converter 43. The detection signal amplifier 42 amplifies the detection signals Vdet. The A/D converter 43 converts analog signals output from the detection signal amplifier 42 into digital signals.

The signal processor 44 is a logic circuit that detects a predetermined physical quantity received by the sensor 10 based on an output signal of the detection circuit 48. When the finger is in contact with or in proximity to a detection surface, the signal processor 44 can detect the asperities on the surface of the finger or the palm based on the signal from the detection circuit 48. The signal processor 44 can also detect the information on the living body based on the signal from the detection circuit 48. Examples of the information on the living body include the vascular image, the pulse wave, the pulsation, and the blood oxygen level of the finger or the palm.

The signal processor 44 may also perform processing of acquiring the detection signals Vdet (information on the living body) simultaneously detected by the photodiodes PD, and averaging the detection signals Vdet. In this case, the detector 40 can perform stable detection by reducing measurement errors caused by noise or relative positional misalignment between the object Fg to be detected, such as the finger, and the sensor 10.

The storage 46 temporarily stores therein signals calculated by the signal processor 44. The storage 46 may be, for example, a random-access memory (RAM) or a register circuit.

The coordinate extractor 45 is a logic circuit that obtains detected coordinates of the asperities on the surface of the finger or the like when the contact or the proximity of the finger is detected by the signal processor 44. The coordinate extractor 45 is also a logic circuit that obtains detected coordinates of blood vessels of the finger or the palm. The image processor 49 combines the detection signals Vdet output from the respective photodiodes PD of the sensor 10 to generate two-dimensional information representing the shape of the asperities on the surface of the finger or the like and two-dimensional information representing the shape of the blood vessels of the finger or the palm. The coordinate extractor 45 may output the detection signals Vdet as sensor output voltages Vo instead of calculating the detected coordinates. A case can be considered where the detector 40 does not include the coordinate extractor 45 and the image processor 49.

The output processor 50 serves as a processor that performs processing based on the outputs from the photodiodes PD. The output processor 50 may include, for example, the detected coordinates obtained by the coordinate extractor 45 and the two-dimensional information generated by the image processor 49 in the sensor output voltages Vo. The function of the output processor 50 may be integrated into another component (such as the image processor 49).

The following describes a circuit configuration example of the detection device 1. FIG. 4 is a circuit diagram illustrating the detection device. As illustrated in FIG. 4, the sensor 10 includes the detection elements PAA arranged in a matrix having a row-column configuration. Each of the detection elements PAA is provided with the photodiode PD.

The gate lines GCL extend in the first direction Dx, and are coupled to the detection elements PAA arranged in the first direction Dx. A plurality of gate lines GCL(1), GCL(2), . . . , GCL(8) are arranged in the second direction Dy, and are each coupled to the gate line drive circuit 15. In the following description, the gate lines GCL(1), GCL(2), . . . , GCL(8) will each be simply referred to as the gate line GCL when need not be distinguished from one another. For ease of understanding of the description, FIG.

4 illustrates eight of the gate lines GCL. However, this is merely an example, and M (where M is eight or larger, and is, for example, 256) of the gate lines GCL may be arranged.

The signal lines SGL extend in the second direction Dy, and are coupled to the photodiodes PD of the detection elements PAA arranged in the second direction Dy. A plurality of signal lines SGL(1), SGL(2), . . . , SGL(12) are arranged in the first direction Dx, and are each coupled to the signal line selection circuit 16 and a reset circuit 17. In the following description, the signal lines SGL(1), SGL(2), . . . , SGL(12) will each be simply referred to as the signal line SGL when need not be distinguished from one another.

For ease of understanding of the description, 12 of the signal lines SGL are illustrated. However, this is merely an example, and N (where N is 12 or larger, and is, for example, 252) of the signal lines SGL may be arranged. The resolution of the sensor is, for example, 508 dots per inch (dpi), and the number of cells is 252×256. In FIG. 4, the sensor 10 is provided between the signal line selection circuit 16 and the reset circuit 17. The present disclosure is not limited thereto. The signal line selection circuit 16 and the reset circuit 17 may be coupled to ends of the signal lines SGL in the same direction.

The gate line drive circuit 15 receives the various control signals such as the start signal STV, the clock signal CK, and the reset signal RST1 from the control circuit 122 (refer to FIG. 1). The gate line drive circuit 15 sequentially selects the gate lines GCL(1), GCL(2), . . . , GCL(8) in a time-division manner based on the various control signals. The gate line drive circuit 15 supplies the gate drive signal Vgcl to the selected one of the gate lines GCL. This operation supplies the gate drive signal Vgcl to a plurality of first switching elements Tr coupled to the gate line GCL, and corresponding ones of the detection elements PAA arranged in the first direction Dx are selected as detection targets.

The signal line selection circuit 16 includes a plurality of selection signal lines Lsel, a plurality of output signal lines Lout, and third switching elements TrS. The third switching elements TrS are provided correspondingly to the respective signal lines SGL. Six of the signal lines SGL(1), SGL(2), . . . , SGL(6) are coupled to a common output signal line Lout1. Six of the signal lines SGL(7), SGL(8), . . . , SGL(12) are coupled to a common output signal line Lout2. The output signal lines Lout1 and Lout2 are each coupled to the detection circuit 48.

The signal lines SGL(1), SGL(2), . . . , SGL(6) are grouped into a first signal line block, and the signal lines SGL(7), SGL(8), . . . , SGL(12) are grouped into a second signal line block. The selection signal lines Lsel are coupled to the gates of the respective third switching elements TrS included in one of the signal line blocks. One of the selection signal lines Lsel is coupled to the gates of the third switching elements TrS in the signal line blocks.

The control circuit 122 (refer to FIG. 1) sequentially supplies the selection signal ASW to the selection signal lines Lsel. This operation causes the signal line selection circuit 16 to operate the third switching elements TrS to sequentially select the signal lines SGL in one of the signal line blocks in a time-division manner. The signal line selection circuit 16 selects one of the signal lines SGL in each of the signal line blocks. With the above-described configuration, the detection device 1 can reduce the number of integrated circuits (ICs) including the detection circuit 48 or the number of terminals of the ICs. The signal line selection circuit 16 may couple a plurality of the signal lines SGL in a bundle to the detection circuit 48.

As illustrated in FIG. 4, the reset circuit 17 includes a reference signal line Lvr, a reset signal line Lrst, and fourth switching elements TrR. The fourth switching elements TrR are provided correspondingly to the signal lines SGL. The reference signal line Lvr is coupled to either the sources or the drains of the fourth switching elements TrR. The reset signal line Lrst is coupled to the gates of the fourth switching elements TrR.

The control circuit 122 supplies a reset signal RST2 to the reset signal line Lrst. This operation turns on the fourth switching elements TrR to electrically couple the signal lines SGL to the reference signal line Lvr. The power supply circuit 123 supplies a reference signal COM to the reference signal line Lvr. This operation supplies the reference signal COM to a capacitive element Ca (refer to FIG. 5) included in each of the detection elements PAA.

Figure 5:
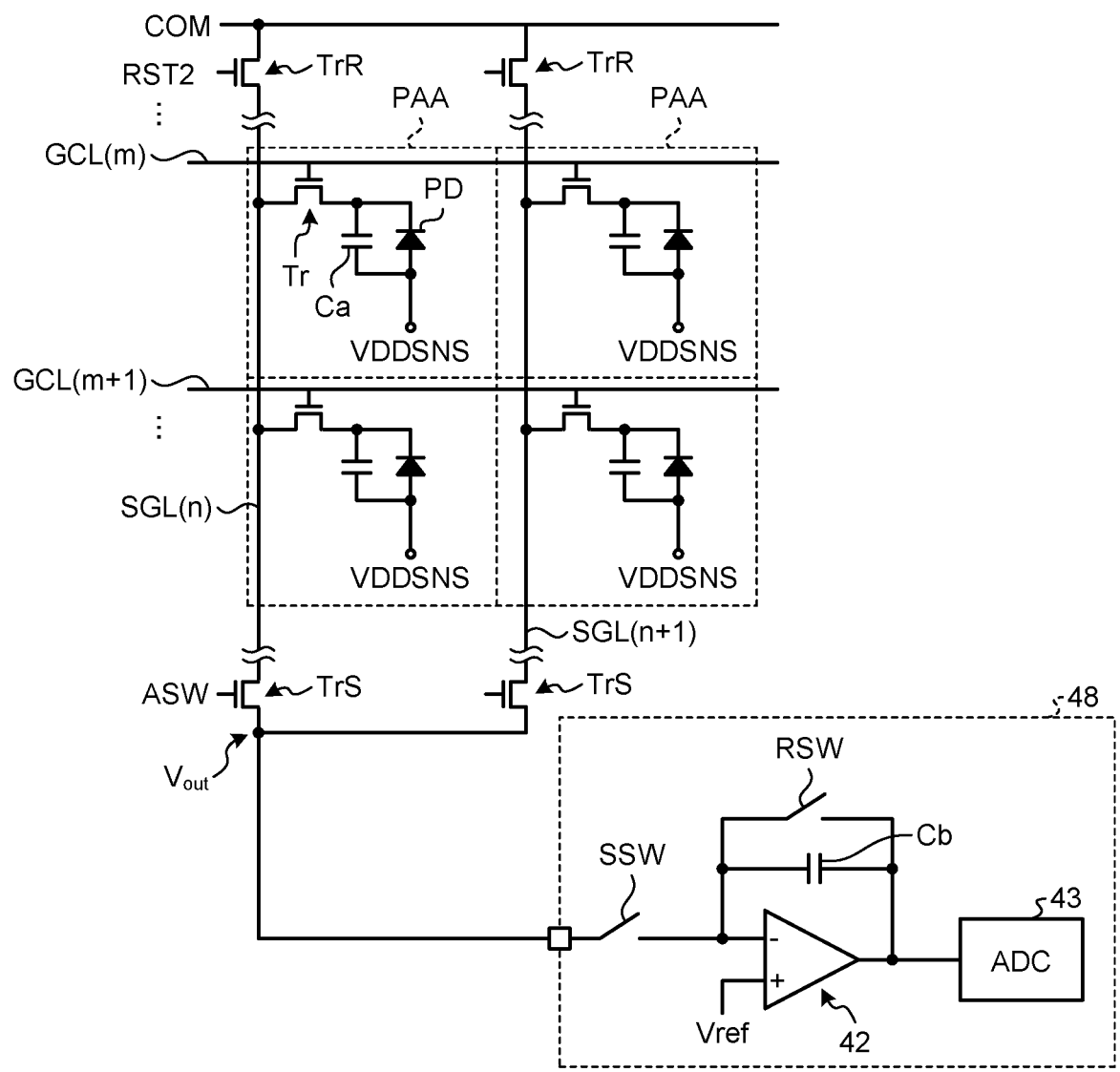
FIG. 5 is a circuit diagram illustrating a plurality of detection elements.

FIG. 5 is a circuit diagram illustrating the detection elements. FIG. 5 also illustrates a circuit configuration of the detection circuit 48. As illustrated in FIG. 5, each of the detection elements PAA includes the photodiode PD, the capacitive element Ca, and a corresponding one of the first switching elements Tr. The capacitive element Ca is capacitance (sensor capacitance) generated in the photodiode PD, and is equivalently coupled in parallel with the photodiode PD.

FIG. 5 illustrates two gate lines GCL(m) and GCL(m+1) arranged in the second direction Dy among the gate lines GCL. FIG. 5 also illustrates two signal lines SGL(n) and SGL(n+1) arranged in the first direction Dx among the signal lines SGL. The detection element PAA is an area surrounded by the gate lines GCL and the signal lines SGL.

Each of the first switching elements Tr is provided correspondingly to the photodiode PD. The first switching element Tr is constituted by a thin-film transistor, and in this example, constituted by an n-channel metal oxide semiconductor (MOS) thin-film transistor (TFT).

The gates of the first switching elements Tr belonging to the detection elements PAA arranged in the first direction Dx are coupled to the gate line GCL. The sources of the first switching elements Tr belonging to the detection elements PAA arranged in the second direction Dy are coupled to the signal line SGL. The drain of the first switching element Tr is coupled to the cathode of the photodiode PD and the capacitive element Ca.

The anode of the photodiode PD is supplied with the sensor power supply signal VDDSNS from the power supply circuit 123. The signal line SGL and the capacitive element Ca are supplied with the reference signal COM that serves as an initial potential of the signal line SGL and the capacitive element Ca from the power supply circuit 123.

When the detection element PAA is irradiated with light, a current corresponding to the amount of the light flows through the photodiode PD. As a result, an electric charge is stored in the capacitive element Ca. After the first switching element Tr is turned on, a current corresponding to the electric charge stored in the capacitive element Ca flows through the signal line SGL. The signal line SGL is coupled to the detection circuit 48 through a corresponding one of the third switching elements TrS of the signal line selection circuit 16. Thus, the detection device 1 can detect a signal corresponding to the amount of the light irradiating the photodiode PD in each of the detection elements PAA or each block unit PAG.

During a reading period, a switch SSW is turned on to couple the detection circuit 48 to the signal line SGL. The detection signal amplifier 42 of the detection circuit 48 converts a variation of a current supplied from the signal line SGL into a variation of a voltage, and amplifies the result. A reference potential (Vref) having a fixed potential is supplied to a non-inverting input terminal (+) of the detection signal amplifier 42, and the signal line SGL is coupled to an inverting input terminal (−) of the detection signal amplifier 42. In the present embodiment, the same signal as the reference signal COM is supplied as the reference potential (Vref). The signal processor 44 (refer to FIG. 3) calculates the difference between the detection signal Vdet when light irradiates the photodiode PD and the detection signal Vdet when light does not irradiate the photodiode PD as each of the sensor output voltages Vo. The detection signal amplifier 42 includes a capacitive element Cb and a reset switch RSW. During a reset period, the reset switch RSW is turned on to reset an electric charge of the capacitive element Cb.

Figure 6:
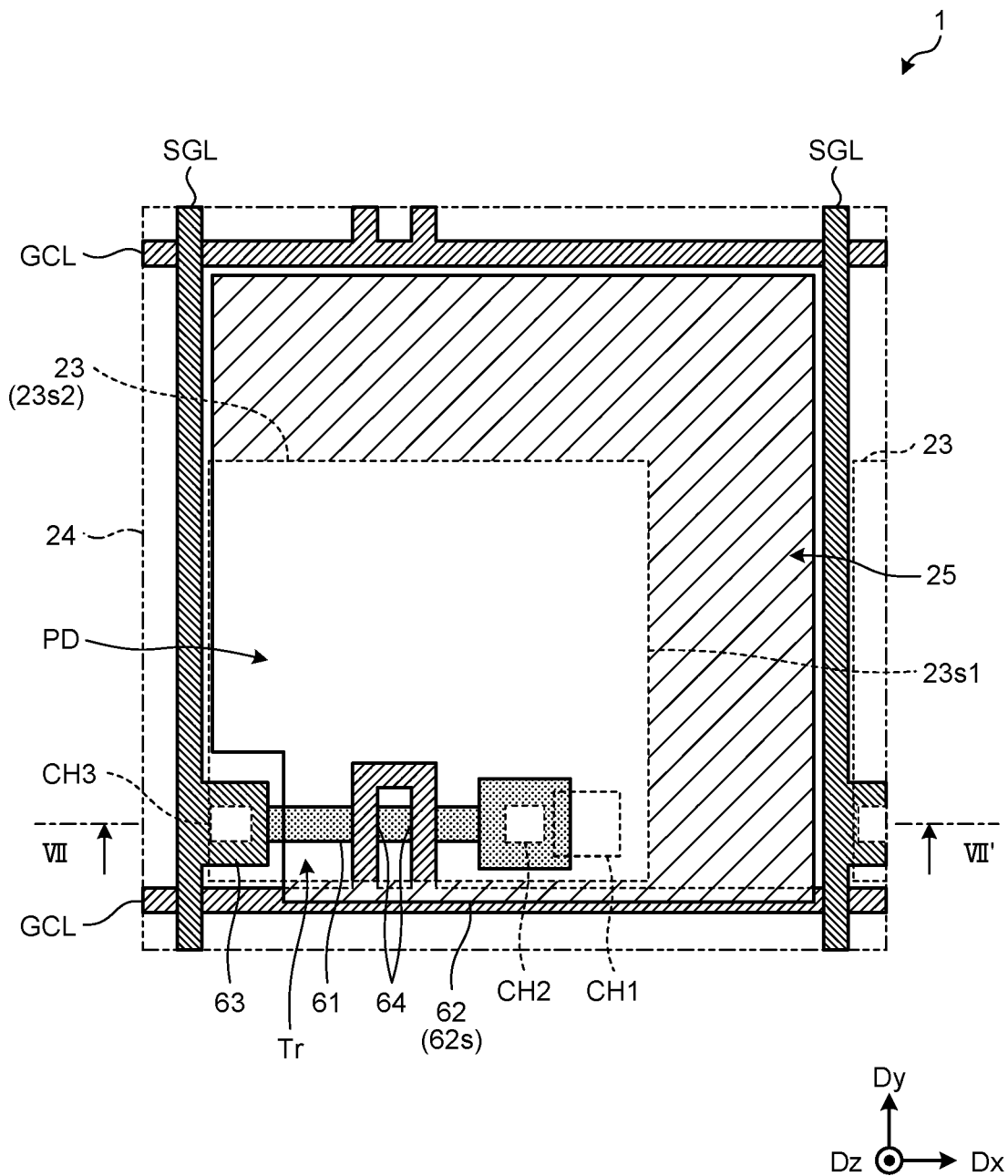
FIG. 6 is a plan view schematically illustrating the detection device according to the first embodiment.

The following describes a configuration of the photodiode PD. FIG. 6 is a plan view schematically illustrating the detection device according to the first embodiment. FIG. 6 illustrates a reflective layer 25 with oblique lines.

As illustrated in FIG. 6, the photodiode PD, a lower electrode 23, the reflective layer 25, and the first switching element Tr are provided in an area surrounded by the gate lines GCL and the signal lines SGL. The lower electrode 23 is a cathode electrode of the photodiode PD, and the photodiodes PD and the lower electrodes 23 are arranged in a matrix having a row-column configuration on the substrate 21.

As illustrated in FIG. 6, the lower electrode 23 is formed to have an area smaller than the area defined by the gate lines GCL and the signal lines SGL, and is provided so as to overlap at least a portion of the first switching element Tr. The lower electrode 23 has a quadrilateral shape including a first side 23s1 extending in the second direction Dy and a second side 23s2 extending in the first direction Dx. The first side 23s1 of the lower electrode 23 and the signal lines SGL are provided so as to be separate from each other in the first direction Dx. The second side 23s2 of the lower electrode 23 and the gate lines GCL are provided so as to be separate from each other in the second direction Dy.

The reflective layer 25 is provided between the lower electrodes 23 adjacent to each other in the plan view. In more detail, the reflective layer 25 is formed so as to be continuously integrated with a source electrode 62 of the first switching element Tr. In the plan view, the reflective layer 25 is provided between the first side 23s1 of the lower electrode 23 and the signal line SGL, and between the second side 23s2 of the lower electrode 23 and the gate line GCL. The reflective layer 25 is provided so as to overlap at least one of the gate lines GCL adjacent to each other in the second direction Dy. In the example illustrated in FIG. 6, an outer edge of the reflective layer 25 is provided so as to overlap the gate line GCL located in a position closer to the first switching element Tr. The reflective layer 25 is provided so as to be separate from the signal lines SGL.

As illustrated in FIG. 6, the first switching element Tr includes a semiconductor layer 61, the source electrode 62, a drain electrode 63, and a gate electrode 64. The semiconductor layer 61 extends along the gate line GCL, and is provided so as to intersect the gate electrodes 64 in the plan view. The gate electrodes 64 are coupled to the gate line GCL, and extend in a direction orthogonal to the gate line GCL. The two gate electrodes 64 are arranged side by side in the first direction Dx. The first switching element Tr of the present embodiment has a double-gate structure in which the two gate electrodes 64 are provided so as to overlap the semiconductor layer 61.

One end side of the semiconductor layer 61 is coupled to the source electrode 62 through a second contact hole CH2. The lower electrode 23 is electrically coupled to the source electrode 62 of the first switching element Tr through a first contact hole CH1. As a result, the first switching element Tr is electrically coupled to the photodiode PD. The other end side of the semiconductor layer 61 is coupled to the drain electrode 63 through a third contact hole CH3. The drain electrode 63 is coupled to the signal line SGL.

The configuration and the arrangement of the first switching element Tr illustrated in FIG. 6 are merely exemplary, and can be changed as appropriate.

Figure 7:
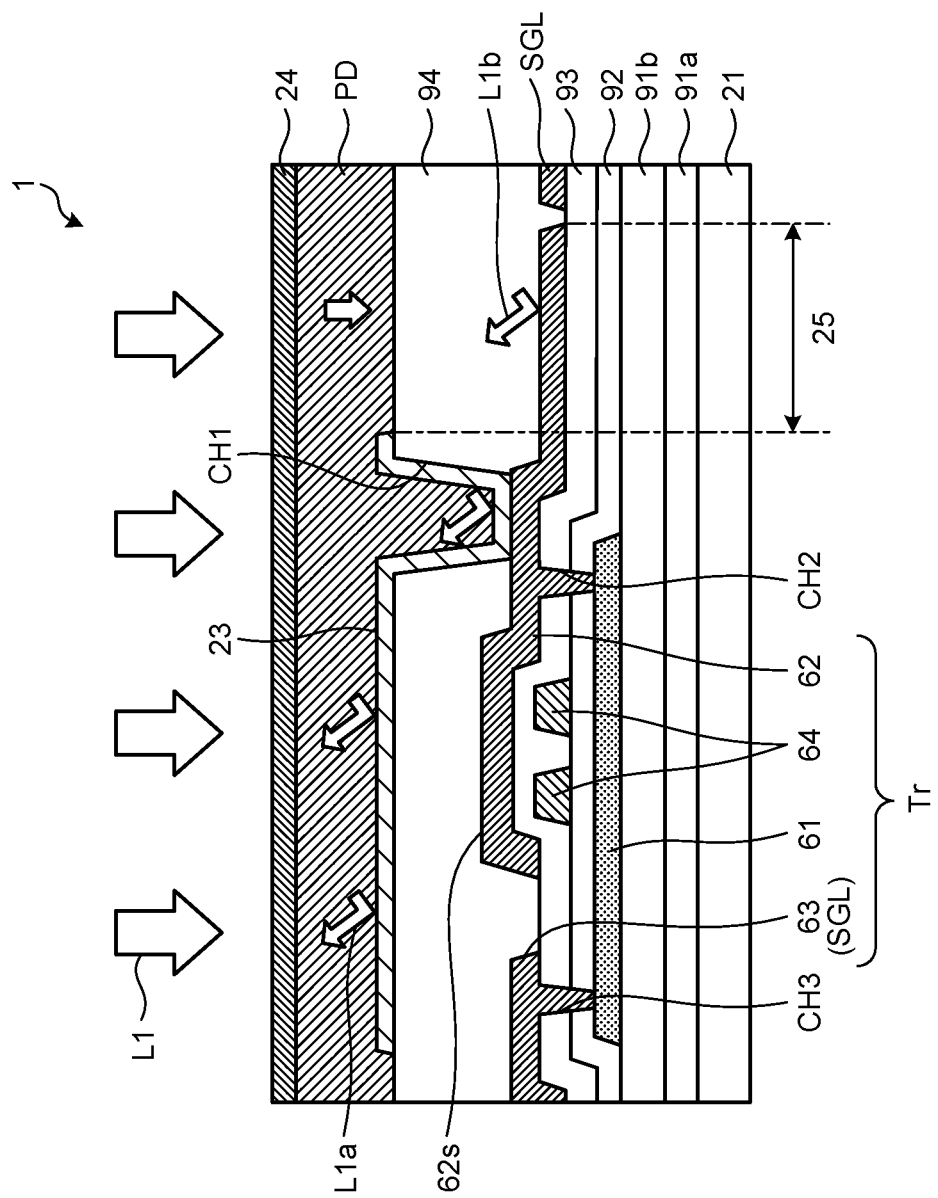
FIG. 7 is a VII-VII' sectional view of FIG. 6.

FIG. 7 is a VII-VII' sectional view of FIG. 6. As illustrated in FIG. 7, the detection device 1 includes the substrate 21, the first switching element Tr, an organic insulating film 94, the lower electrode 23, the photodiode PD, an upper electrode 24, and the reflective layer 25. Although not illustrated in FIG. 7, a sealing film covering the photodiode PD and the upper electrode 24 is provided as needed.

The substrate 21 is an insulating base material, and is made using, for example, glass or a resin material. The substrate 21 is not limited to having a flat plate shape, and may have a curved surface. In this case, the substrate 21 may be a film-like resin.

In this specification, a direction from the substrate 21 toward the photodiode PD in a direction orthogonal to a surface of the substrate 21 is referred to as "upper side" or simply "above". A direction from the photodiode PD toward the substrate 21 is referred to as "lower side" or simply "below".

Undercoat films 91a and 91b are provided above the substrate 21. The undercoat films 91a and 91b are each formed of, for example, an inorganic insulating film such as a silicon nitride film or a silicon oxide film. The undercoat films 91a and 91b are not limited to being configured as a multilayered film having two stacked layers of inorganic insulating films, and may be three or more layers, or alternatively be a single-layer film. A light-blocking film may be provided between the substrate 21 and the semiconductor layer 61.

The first switching elements Tr (transistors) are provided above the substrate 21. Each of the first switching elements Tr is provided by stacking the semiconductor layer 61, the gate electrodes 64, the source electrode 62, and the drain electrode 63 in this order above the substrate 21. More specifically, the semiconductor layer 61 is provided above the undercoat film 91b. For example, polysilicon is used as the semiconductor layer 61. The semiconductor layer 61 is, however, not limited thereto, and may be formed of, for example, a microcrystalline oxide semiconductor, an amorphous oxide semiconductor, or low-temperature polysilicon. Although only an n-type TFT is illustrated as the first switching element Tr, a p-type TFT may be formed at the same time.

A gate insulating film 92 is provided above the undercoat film 91b so as to cover the semiconductor layer 61. The gate insulating film 92 is, for example, an inorganic insulating film such as a silicon oxide film. The gate electrodes 64 are provided above the gate insulating film 92. In the example illustrated in FIG. 7 the first switching element Tr has a top-gate structure. However, the first switching element Tr is not limited thereto, and may have a bottom-gate structure, or a dual-gate structure in which the gate electrodes 64 are provided both above and below the semiconductor layer 61.

An interlayer insulating film 93 is provided above the gate insulating film 92 so as to cover the gate electrodes 64. The interlayer insulating film 93 has, for example, a multilayered structure of a silicon nitride film and a silicon oxide film. The source electrode 62 and the drain electrode 63 are provided above the interlayer insulating film 93. The source electrode 62 is coupled to a source area of the semiconductor layer 61 through the second contact hole CH2 provided in the gate insulating film 92 and the interlayer insulating film 93. The drain electrode 63 is coupled to a drain area of the semiconductor layer 61 through the third contact hole CH3 provided in the gate insulating film 92 and the interlayer insulating film 93.

An overlapping portion 62s is formed continuously with the source electrode 62, and is provided in an area that is in the same layer as the source electrode 62 and overlaps the gate electrodes 64. In other words, a portion of the source electrode 62 that overlaps the gate electrodes 64 can be denoted as the overlapping portion 62s. The overlapping portion 62s can restrain the light L1 from irradiating the semiconductor layer 61.

The reflective layer 25 is formed continuously with the source electrode 62, and is provided in the same layer as that of the source electrode 62, that is, between the interlayer insulating film 93 and the organic insulating film 94. In other words, a portion of the source electrode 62 that does not overlap the lower electrode 23 can be denoted as the reflective layer 25.

The organic insulating film 94 is provided above the interlayer insulating film 93 so as to cover the source electrode 62 and the drain electrode 63 of the first switching element Tr. The organic insulating film 94 is an organic planarizing film, and has a better coverage property for wiring steps and provides better surface flatness than inorganic insulating materials formed by, for example, chemical vapor deposition (CVD).

The photodiodes PD are provided above the organic insulating film 94. The lower electrode 23 is provided between both the substrate 21 and the organic insulating film 94 and the photodiode PD in the direction orthogonal to the surface of the substrate 21.

In more detail, the lower electrode 23 is provided above the organic insulating film 94, and is provided so as to cover the bottom surface and the inner side surface of the first contact hole CH1 formed in the organic insulating film 94. The lower electrode 23 is coupled to the source electrode 62 of the first switching element Tr on the bottom surface of the first contact hole CH1. The lower electrode 23 is the cathode electrode of the photodiode PD, and is formed of a metal material such as silver (Ag). As a result, the lower electrode 23 serves as a reflective electrode. The lower electrodes 23 are arranged so as to be separated for each of the detection elements PAA (photodiodes PD). The photodiode PD has a larger area than that of the lower electrode 23 in the plan view, and covers the upper surface and outer edges of the lower electrode 23.

The photodiodes PD are provided so as to cover the lower electrodes 23 and the organic insulating film 94. Although not illustrated in FIG. 7, the photodiode PD has a configuration in which, for example, an electron transport layer (first carrier transport layer), an active layer, and a hole transport layer (second carrier transport layer) are stacked between the lower electrode 23 and the upper electrode 24.

The electron transport layer is formed by coating using a material such as zinc acetate, ethoxylated polyethylenimine (PEIE), or polyethylenimine (PEI).

A mixture of a p-type organic semiconductor and an n-type organic semiconductor is used as the active layer. poly((2,5-bis(2-hexyldecyl)-2,3,5,6-tetrahydro-3,6-di-oxopyrrolo(3,4-c)pyrrole-1,4-diyl)-alt-(3',3"-dimethyl-2,2': 5',2"-terthiophene)-5,5"-diyl) (PMDPP3T) is an example of the p-type organic semiconductor. [6,6]-phenyl C61-butyric acid methyl ester (PC61BM) is an example of the n-type organic semiconductor. Alternatively, the active layer may be formed using a material such as P3HT:PC61BM or PTB7:PC71BM.

The hole transport layer is, for example, a metal oxide layer of, for example, tungsten oxide ($WO_3$) or a molybdenum oxide (MoOx). The hole transport layer is formed of a vapor-deposited film or a sputtered film. Alternatively, the hole transport layer may be formed by coating using a material such as PEDOT:PSS.

The electron transport layer, the active layer, and the hole transport layer forming the photodiodes PD are continuously provided so as to cover the lower electrodes 23. In other words, the photodiode PD includes a portion overlapping the lower electrode 23 and a portion provided above the organic insulating film 94 in an area not overlapping the lower electrode 23.

The upper electrode 24 is provided across above the photodiodes PD. The upper electrode 24 is an anode electrode of the photodiodes PD, and is continuously formed over the detection elements PAA (photodiodes PD). The upper electrode 24 is formed of, for example, a light-transmitting conductive material such as indium tin oxide (ITO) or indium zinc oxide (IZO).

As described above, the detection device 1 of the present embodiment includes the substrate 21, the photodiodes PD provided on the substrate 21, the first switching elements Tr (transistors) provided correspondingly to the respective photodiodes PD, the gate lines GCL extending in the first direction Dx, the signal lines SGL extending in the second direction Dy intersecting the first direction Dx, the lower electrodes 23 that are provided between the transistors and the photodiodes PD in the direction orthogonal to the substrate 21, and are provided correspondingly to the respective photodiodes PD, the upper electrode 24 provided across the photodiodes PD, and the reflective layer 25 provided between the substrate 21 and the photodiodes PD in the direction orthogonal to the substrate 21. The lower electrode 23 has a smaller area than the area defined by the gate lines GCL and the signal lines SGL, and the reflective layer 25 is provided between the lower electrodes 23 adjacent to each other in the plan view.

In the detection device 1 of the present embodiment, the first switching element Tr (transistor) includes the semiconductor layer 61, the gate electrodes 64, and the source electrode 62, and is provided by stacking the semiconductor layer 61, the gate electrodes 64, and the source electrode 62 in this order in the direction orthogonal to the substrate 21. The reflective layer 25 is provided in the same layer as that of the source electrode 62.

With this configuration, in the detection device 1, the light L1 transmitted through the object Fg to be detected (refer to FIG. 2) irradiates the photodiode PD. In an area overlapping the lower electrode 23, components of the light L1 that have not been absorbed by the photodiode PD are reflected by the lower electrode 23. A portion of reflected light L1a reflected by the lower electrode 23 is absorbed by the photodiode PD.

In an area not overlapping the lower electrode 23 (area between the adjacent lower electrodes 23), the light L1 transmitted through the photodiode PD, that is, components of the light L1 that have not been absorbed by the photodiode PD are reflected by the reflective layer 25. Reflected light L1b reflected by the reflective layer 25 travels upward (toward the photodiode PD), and a portion of the reflected light Lib is absorbed by the photodiode PD. Thus, the detection device 1 of the present embodiment can improve the use efficiency of the light L1 in the area between the adjacent lower electrodes 23 by being provided with the reflective layer 25.

Since the outer edge of the reflective layer 25 is provided so as to overlap the gate line GCL, a gap between the reflective layer 25 and the gate line GCL can be reduced in the plan view. The reflective layer 25 can effectively reflect the light L1 in the area surrounded by the gate lines GCL and the signal lines SGL, and as a result, can improve the use efficiency of the light L1. The reflective layer 25 also serves as a light-blocking layer that restrains outside light from entering the photodiode PD from the substrate 21 side. The detection device 1 can reduce noise components caused by the outside light emitted from between the adjacent lower electrodes 23.

Second Embodiment

Figure 8:
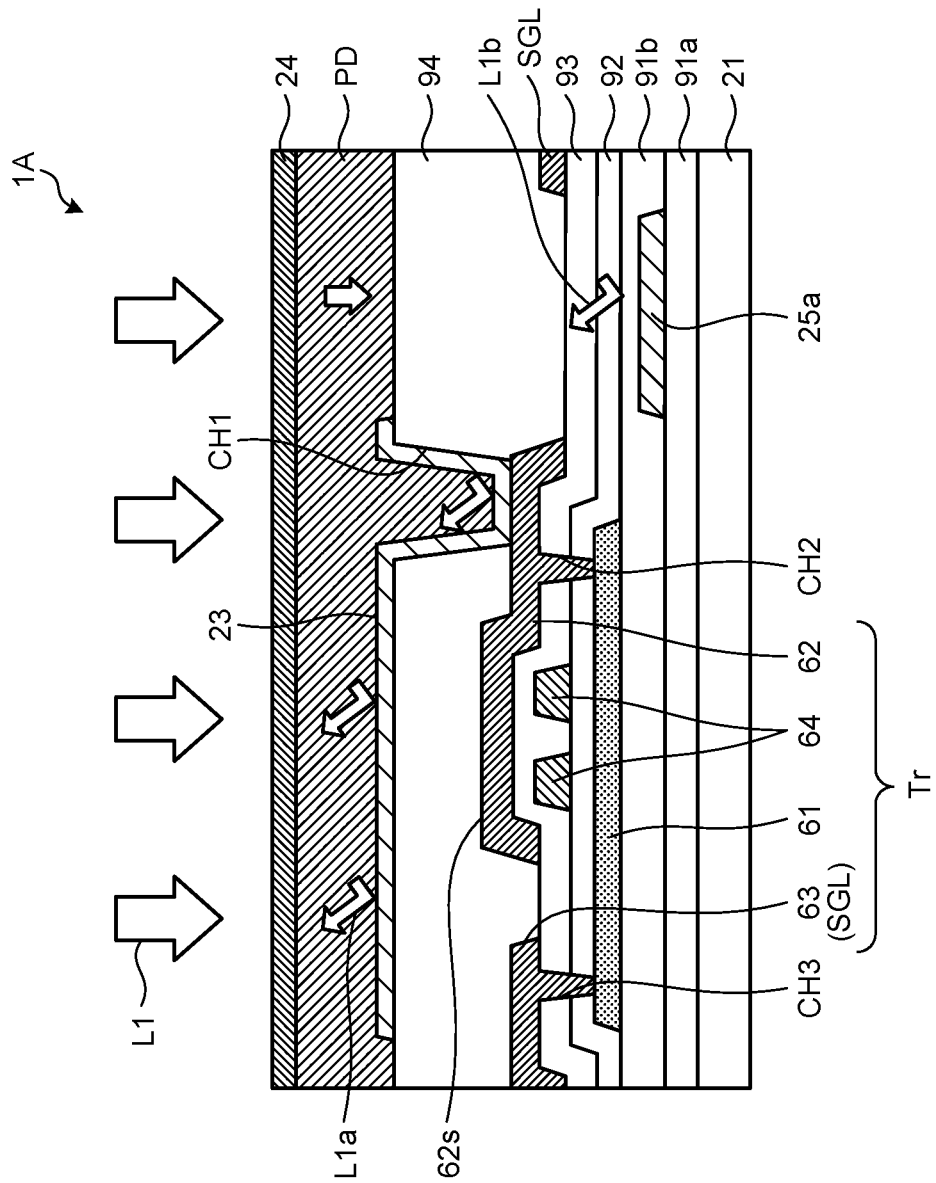
FIG. 8 is a sectional view schematically illustrating a section of a detection device according to a second embodiment.

FIG. 8 is a sectional view schematically illustrating a section of a detection device according to a second embodiment. In the following description, the same components as those described in the embodiment above are denoted by the same reference numerals, and the description thereof will not be repeated.

In the first embodiment described above, the configuration has been described in which the reflective layer 25 is provided in the same layer as that of the source electrode 62. However, the reflective layer 25 is not limited to this configuration, and may be provided in a layer different from that of the source electrode 62, that is, in any layer between the substrate 21 and the photodiode PD.

As illustrated in FIG. 8, in a detection device 1A according to the second embodiment, a reflective layer 25a is provided in a layer between the substrate 21 and the semiconductor layer 61 of the first switching element Tr in the direction orthogonal to the substrate 21. More specifically, the reflective layer 25a is provided above the undercoat film 91a. The undercoat film 91b is provided above the undercoat film 91a so as to cover the reflective layer 25a.

In the example illustrated in FIG. 8, the reflective layer 25a is provided in an area not overlapping the lower electrode 23, and is provided individually for each of the detection elements PAA (photodiodes PD). Although not illustrated in a drawing, the reflective layer 25a is provided between the lower electrodes 23 adjacent to each other in the plan view, in the same manner as in FIG. 6. However, since the reflective layer 25a is provided in a layer different from those of the source electrode 62 (signal line SGL) and the gate electrodes 64 (gate line GCL), the arrangement of the reflective layer 25a is less restricted by these electrodes, wiring, and the like. That is, the reflective layer 25a may be provided so as to overlap at least a portion of the signal line SGL or the gate line GCL in the plan view (refer to FIGS. 6 and 10), or may be provided so as to be separate from the signal line SGL and gate line GCL.

Modification of Second Embodiment

Figure 9:
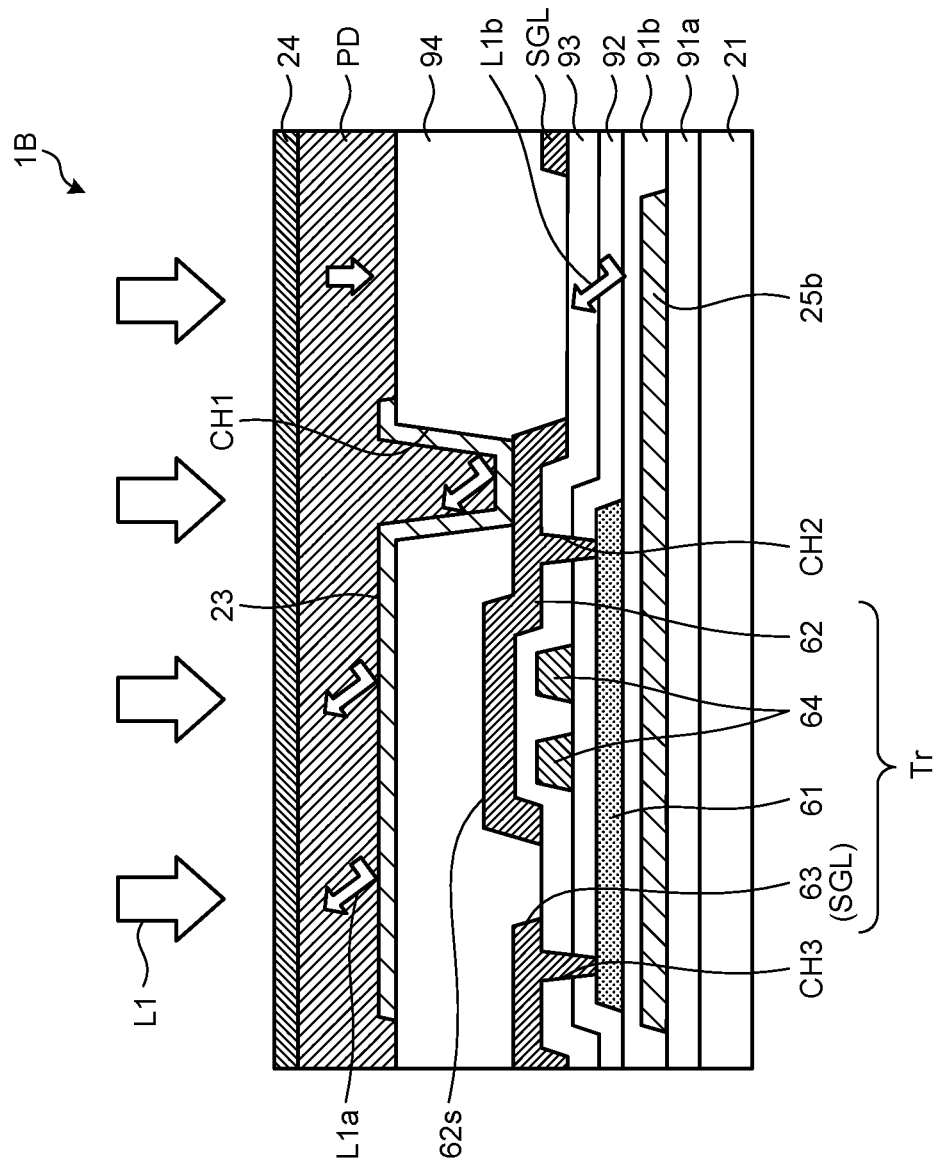
FIG. 9 is a sectional view schematically illustrating a section of a detection device according to a modification of the second embodiment.

FIG. 9 is a sectional view schematically illustrating a section of a detection device according to a modification of the second embodiment. As illustrated in FIG. 9, in a detection device 1B according to the modification of the second embodiment, a reflective layer 25b is provided so as to extend from an area not overlapping the lower electrode 23 to an area overlapping the first switching element Tr and the lower electrode 23. In the area overlapping the first switching element Tr, the reflective layer 25b is provided below the semiconductor layer 61 in the direction orthogonal to the substrate 21, that is, between the substrate 21 and the semiconductor layer 61.

The reflective layer 25b is formed in the area overlapping the entire semiconductor layer 61 and the lower electrode 23, and is also formed in an area overlapping at least a portion of the signal line SGL. In the present modification, the reflective layer 25b also serves as a light-blocking layer that restrains light from entering the semiconductor layer 61 from the substrate 21 side.

The reflective layer 25b may be provided so as to overlap at least a portion of the signal line SGL or the gate line GCL in the plan view (refer to FIGS. 6 and 10), or may be provided so as to be separate from the signal line SGL and gate line GCL. The reflective layer 25b may be continuously formed over the detection elements PAA (photodiodes PD).

Third Embodiment

Figure 10:
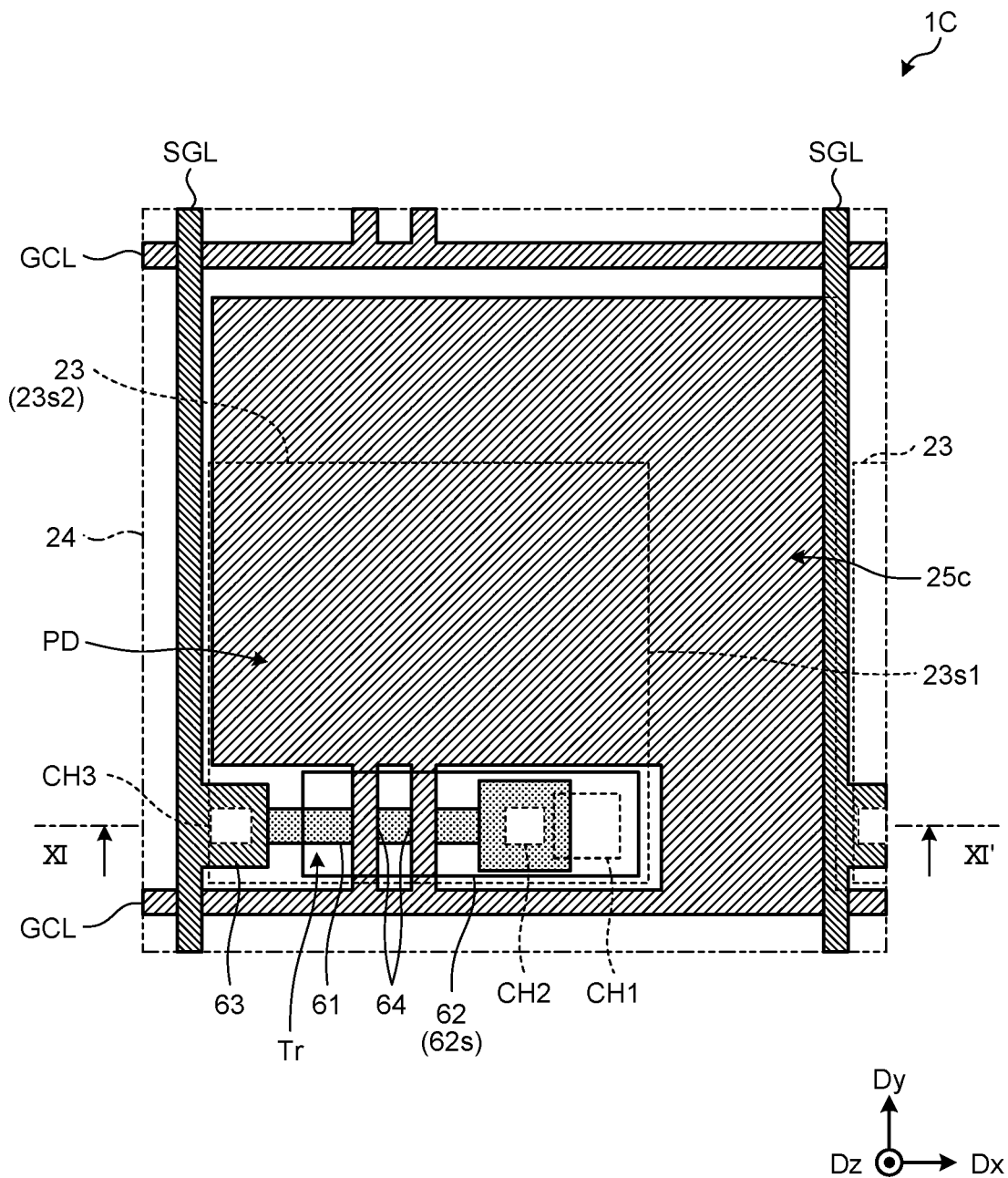
FIG. 10 is a plan view schematically illustrating a detection device according to a third embodiment.
Figure 11:
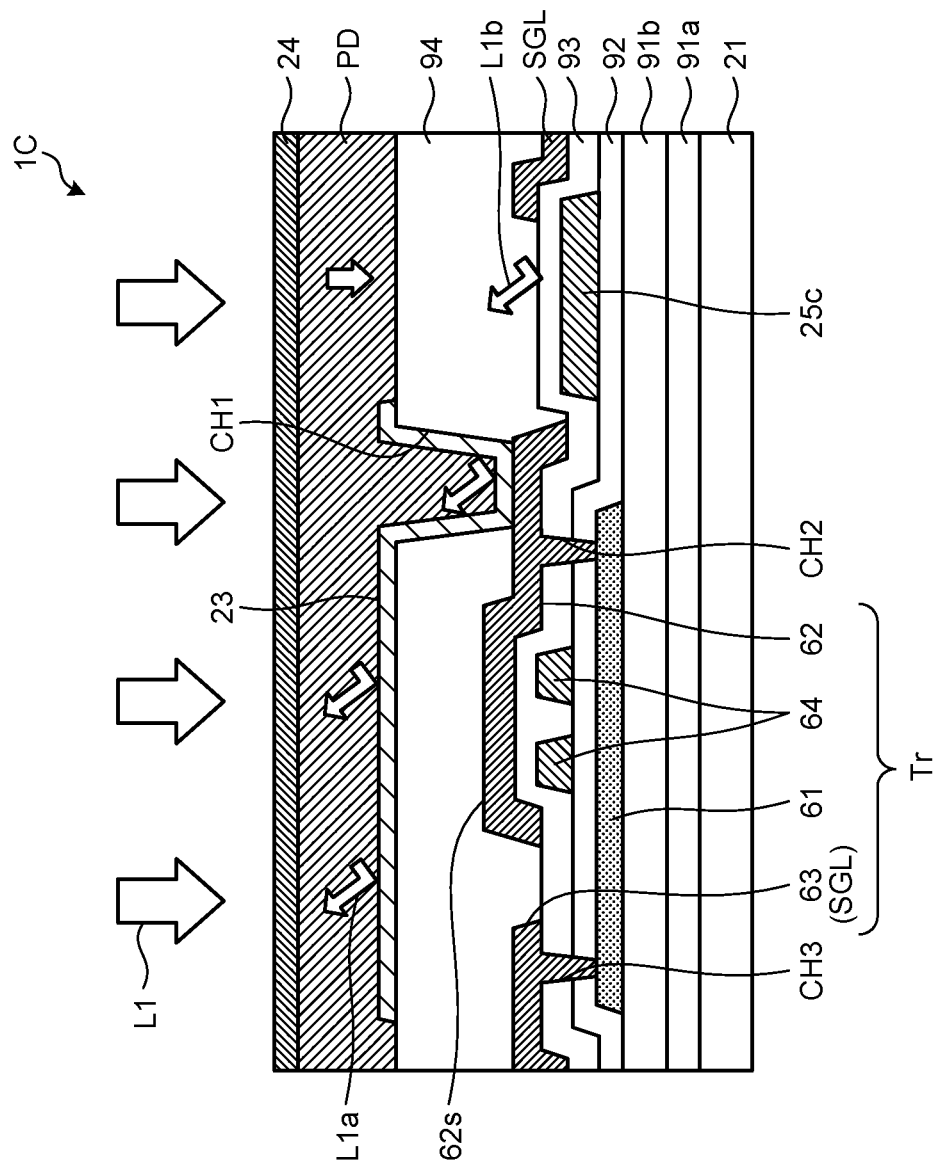
FIG. 11 is an XI-XI' sectional view of FIG. 10.

FIG. 10 is a plan view schematically illustrating a detection device according to a third embodiment. FIG. 11 is an XI-XI' sectional view of FIG. 10. As illustrated in FIGS. 10 and 11, in a detection device 1C according to the third embodiment, a reflective layer 25c is provided in the same layer as that of the gate electrodes 64.

As illustrated in FIG. 10, the reflective layer 25c is formed so as to be continuously integrated with the gate electrodes 64 and the gate line GCL. The reflective layer 25c is coupled to one of the gate lines GCL in a position closer to the first switching element Tr, and is provided so as to be separate from the other of the gate lines GCL in a position farther from the first switching element Tr. The reflective layer 25c is provided so as to overlap at least one of the signal lines SGL adjacent to each other in the first direction Dx in the plan view. More specifically, an outer edge of the reflective layer 25c is provided so as to overlap one of the signal lines SGL adjacent to the first side 23s1 of the lower electrode 23.

In other words, the reflective layer 25c is provided so as to cover most of the area defined by the gate lines GCL and the signal lines SGL, and has openings formed in areas overlapping the semiconductor layer 61, the source electrode 62, and the drain electrode 63 of the first switching element Tr.

As illustrated in FIG. 11, the reflective layer 25c is provided between the gate insulating film 92 and the interlayer insulating film 93. That is, the reflective layer 25c and the gate electrode 64 are provided above the gate insulating film 92. The interlayer insulating film 93 is provided above the gate insulating film 92 so as to cover the gate electrodes 64.

With the configuration describe above, in the present embodiment, the reflective layer 25c covers most of the area that does not overlap the lower electrode 23, and thus can effectively reflect the light L1 transmitted through the photodiode PD.

Fourth Embodiment

Figure 12:
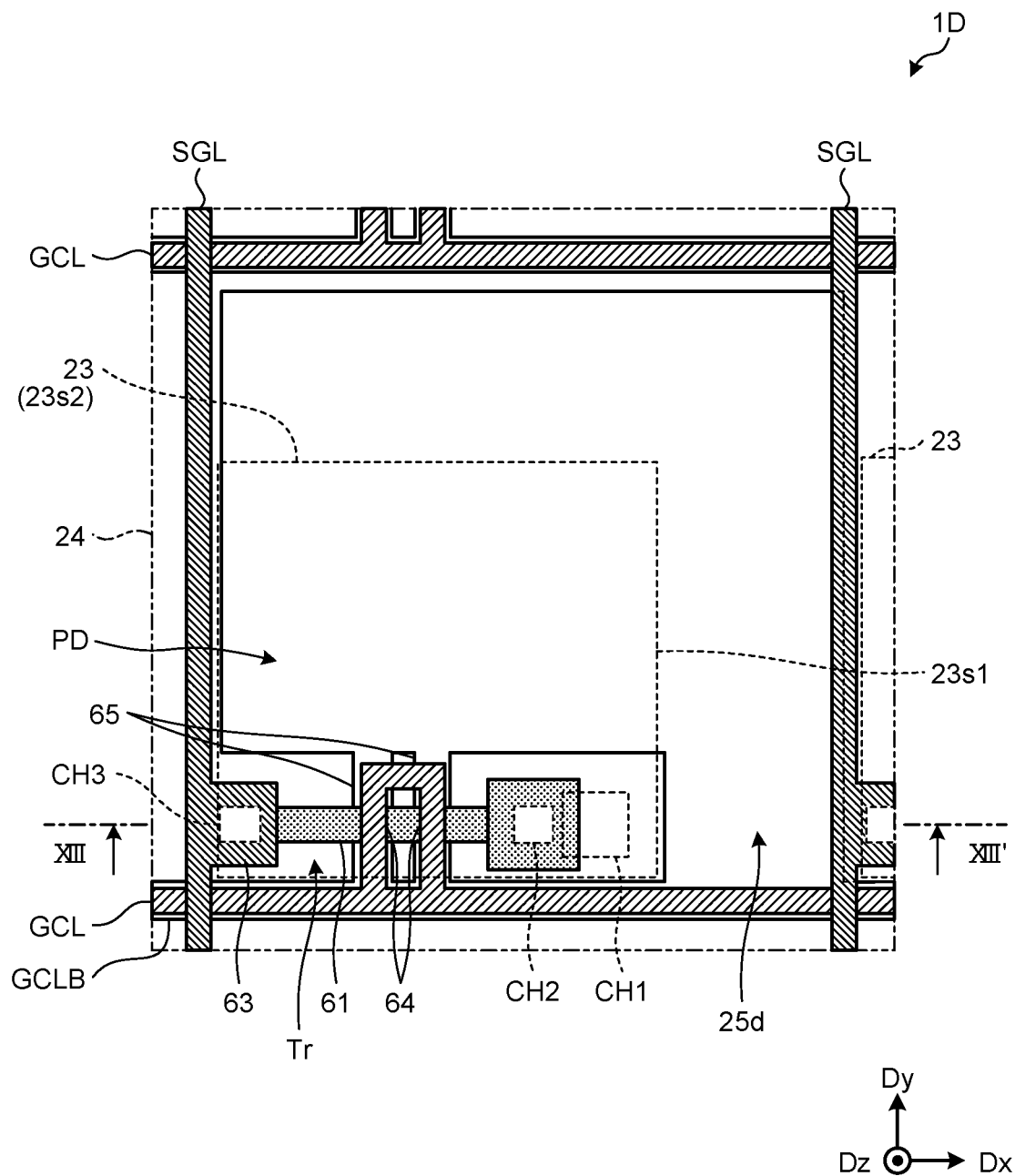
FIG. 12 is a plan view schematically illustrating a detection device according to a fourth embodiment.
Figure 13:
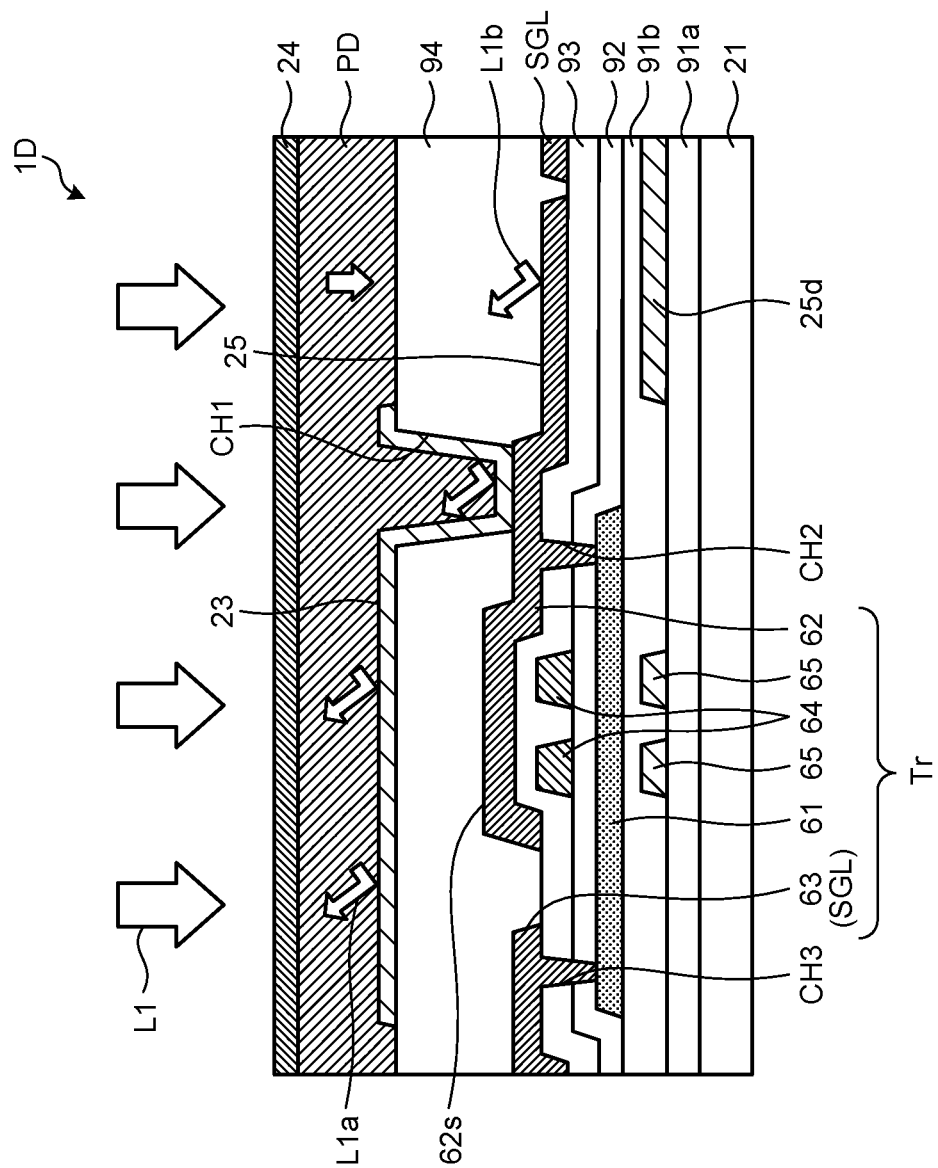
FIG. 13 is a XIII-XIII' sectional view of FIG. 12.

FIG. 12 is a plan view schematically illustrating a detection device according to a fourth embodiment. FIG. 13 is a XIII-XIII' sectional view of FIG. 12. For ease of viewing the drawing, FIG. 12 does not illustrate the source electrode 62 and the reflective layer 25 (refer to FIG. 6) formed integrally with the source electrode 62. As illustrated in FIGS. 12 and 13, a detection device 1D according to the fourth embodiment further includes bottom gate lines GCLB and bottom gate electrodes 65. In the detection device 1D, a reflective layer 25d is provided in the same layer as that of the bottom gate lines GCLB and the bottom gate electrodes 65.

As illustrated in FIG. 12, the bottom gate lines GCLB are provided below the gate lines GCL, and extend in the first direction Dx along the gate lines GCL. The bottom gate electrodes 65 are coupled to each of the bottom gate lines GCLB, and extend in a direction orthogonal to the bottom gate line GCLB. The two bottom gate electrodes 65 are arranged side by side in the first direction Dx, and are provided so as to overlap the semiconductor layer 61. The two bottom gate electrodes 65 are provided below the respective gate electrodes 64.

The reflective layer 25d is formed so as to be continuously integrated with the bottom gate electrodes 65 and the bottom gate line GCLB. The reflective layer 25d is coupled to one of the bottom gate lines GCLB in a position closer to the first switching element Tr, and is provided so as to be separate from the other of the bottom gate lines GCLB in a position farther from the first switching element Tr. The reflective layer 25d is provided so as to overlap at least one of the signal lines SGL adjacent to each other in the first direction Dx in the plan view. More specifically, an outer edge of the reflective layer 25d is provided so as to overlap one of the signal lines SGL adjacent to the first side 23s1 of the lower electrode 23.

In other words, the reflective layer 25d is provided so as to cover most of the area defined by the gate lines GCL and the signal lines SGL, and has openings formed in areas overlapping the semiconductor layer 61, the source electrode 62, and the drain electrode 63 of the first switching element Tr.

As illustrated in FIG. 13, the first switching element Tr is provided by stacking the bottom gate electrodes 65, the semiconductor layer 61, the gate electrodes 64 (top gate electrodes), the source electrode 62, and the drain electrode 63 in this order in the direction orthogonal to the substrate 21. That is, the first switching element Tr of the present embodiment has a dual-gate structure.

As described above, in the detection device 1D, the reflective layer 25d is provided in the same layer as that of the bottom gate electrodes 65. The bottom gate electrodes 65 and the reflective layer 25d are provided above the undercoat film 91a. The undercoat film 91b is provided above the undercoat film 91a so as to cover the bottom gate electrodes 65 and the reflective layer 25d. The bottom gate line GCLB is electrically coupled to the gate line GCL at any location, and the bottom gate electrodes 65 are supplied with the gate drive signal Vgcl that has the same potential as that of the gate electrode 64.

In an area not overlapping the lower electrode 23, the reflective layer 25 is provided above the reflective layer 25d with the undercoat film 91b, the gate insulating film 92, and the interlayer insulating film 93 interposed therebetween. The configuration of the source electrode 62 and the reflective layer 25 is the same as that in the first embodiment described above, and will not be described again. The detection device 1D of the present embodiment includes two layers of the reflective layer 25 and the reflective layer 25d, and thereby can effectively reflect the light L1 transmitted through the photodiode PD.

With the configuration described above, the reflective layer 25d is provided so as to cover most of the area not overlapping the lower electrode 23, and thus can effectively reflect the light L1 transmitted through the photodiode PD.

Fifth Embodiment

Figure 14:
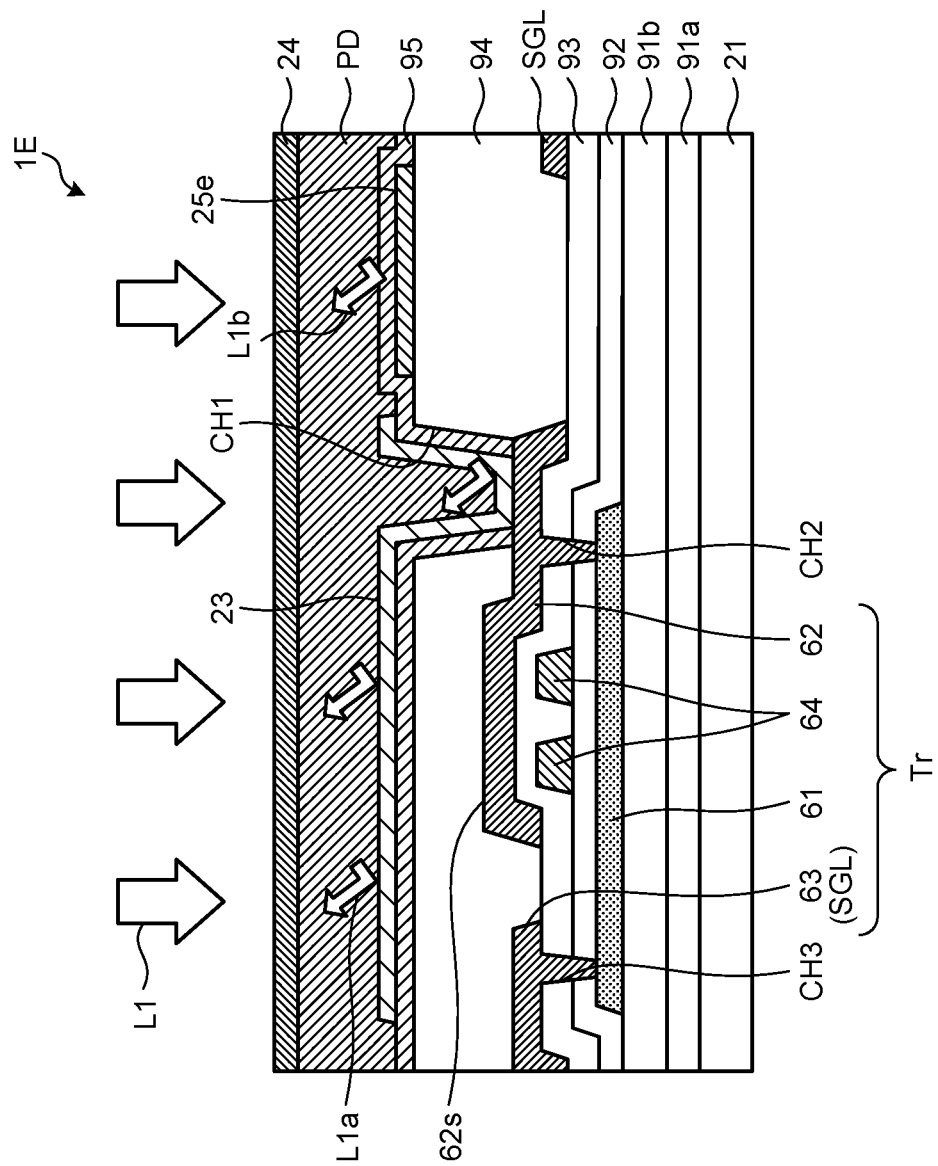
FIG. 14 is a sectional view schematically illustrating a section of a detection device according to a fifth embodiment.

FIG. 14 is a sectional view schematically illustrating a section of a detection device according to a fifth embodiment. As illustrated in FIG. 14, a detection device 1E according to the fifth embodiment includes an inorganic insulating film 95 provided above the organic insulating film 94. The inorganic insulating film 95 is, for example, an inorganic insulating material such as a silicon nitride film or a silicon oxide film. The organic insulating film 94 and the inorganic insulating film 95 are provided so as to cover the first switching element Tr. The inorganic insulating film 95 covers the inner side surface of the first contact hole CH1 formed in the organic insulating film 94, and has an opening in an area overlapping the bottom of the first contact hole CH1.

The lower electrode 23 and the photodiode PD are provided above the inorganic insulating film 95, and are electrically coupled to the source electrode 62 of the first switching element Tr through the first contact hole CH1. That is, the inorganic insulating film 95 is provided between the organic insulating film 94 and the lower electrode 23.

In the present embodiment, a reflective layer 25e is provided between the organic insulating film 94 and the inorganic insulating film 95 in an area not overlapping the lower electrode 23. That is, in the area provided with the reflective layer 25e, the organic insulating film 94, the reflective layer 25e, the inorganic insulating film 95, the photodiode PD, and the upper electrode 24 are stacked in this order in the direction orthogonal to the substrate 21. The reflective layer 25e may be provided so as to overlap the gate line GCL or so as to overlap the signal line SGL, in the same manner as in any of the embodiments described above.

In the detection device 1E according to the fifth embodiment, the reflective layer 25e is provided closer to the photodiode PD than in the first to the fourth embodiments described above. That is, in the direction orthogonal to the substrate 21, the organic insulating film 94 is not provided between the photodiode PD and the reflective layer 25e, and the photodiode PD faces the reflective layer 25e with the inorganic insulating film 95 thinner than the organic insulating film 94 interposed therebetween.

With this configuration, the reflected light L1b reflected by the reflective layer 25e is efficiently returned toward the photodiode PD while being restrained from generating stray light or the like. Accordingly, the detection device 1E can improve the use efficiency of the light L1.

The reflective layer 25e of the present embodiment can be combined with any of the reflective layers 25, 25a, 25b, 25c, and 25d of the first to fourth embodiments described above. As an example, the reflective layer 25 (refer to FIG. 7) provided in the same layer as that of the source electrode 62 may be provided below the reflective layer 25e. Alternatively, the inorganic insulating film 95 of the present embodiment may be provided in the first to the fourth embodiments described above.

In each of the embodiments described above, the example of the photodiode PD has been described in which the lower electrode 23 serves as the cathode electrode of the photodiode PD and the upper electrode 24 serves as the anode electrode of the photodiode PD. However, the photodiode PD is not limited to this example. The lower electrode 23 may serve as the anode electrode of the photodiode PD, and the upper electrode 24 may serve as the cathode electrode of the photodiode PD.

Sixth Embodiment

Figure 15:
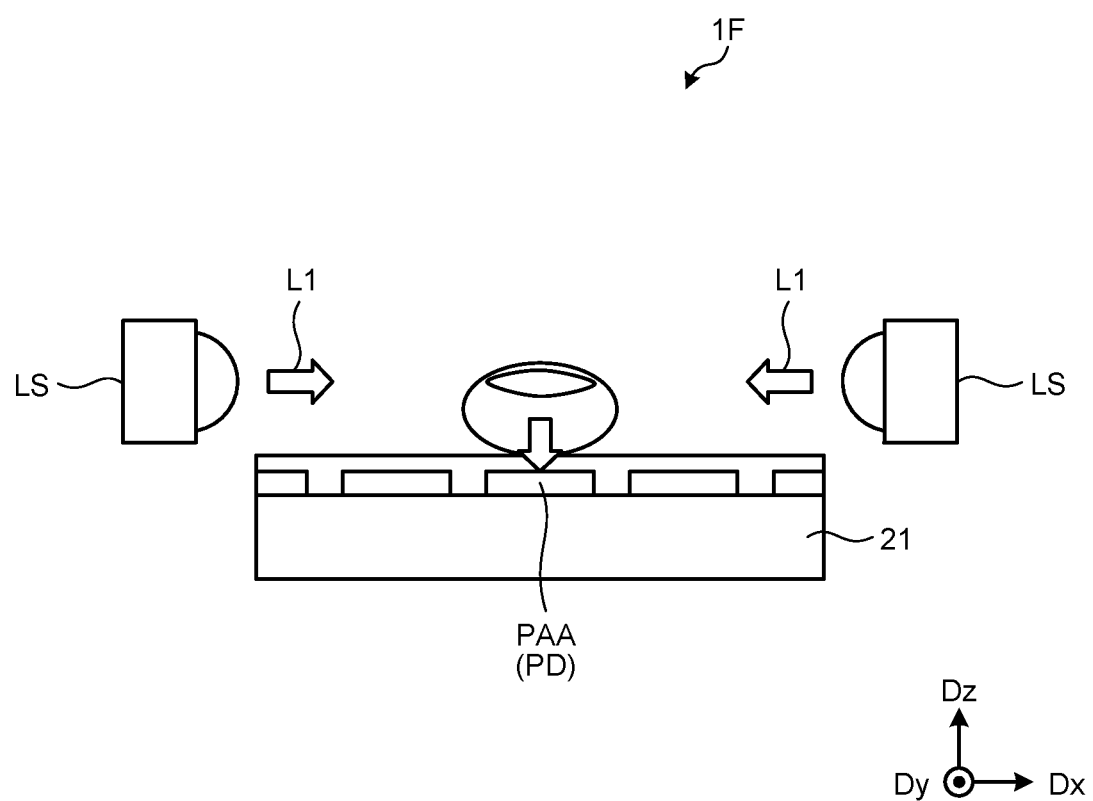
FIG. 15 is a sectional view illustrating a schematic sectional configuration of a detection device according to a sixth embodiment.

FIG. 15 is a sectional view illustrating a schematic sectional configuration of a detection device according to a sixth embodiment. In the first to the fifth embodiments described above, the transmissive detection devices 1 and 1A to 1E have been described. However, the present disclosure is not limited thereto. As illustrated in FIG. 15, a detection device 1F according to the sixth embodiment is a reflective detection device. Specifically, the two light sources LS are provided on lateral sides of the object Fg to be detected, such as the finger, and are arranged side by side in the first direction Dx with the object Fg to be detected interposed therebetween. The light L1 emitted from the light sources LS travels in the first direction Dx, and is reflected on the surface of or in the object Fg to be detected. The light reflected by the object Fg to be detected irradiates the photodiodes PD. This irradiation allows the photodiodes PD to detect the information on the object Fg to be detected based on the light L1 emitted from the light sources LS.

The positions, number, and the like of the light sources LS illustrated in FIG. 15 are only schematically given, and can be changed as appropriate according to, for example, the characteristics (detection sensitivity) required for the detection device 1F and the detection target.

While the preferred embodiments of the present disclosure have been described above, the present disclosure is not limited to the embodiments described above. The content disclosed in the embodiments is merely an example, and can be variously modified within the scope not departing from the gist of the present disclosure. Any modifications appropriately made within the scope not departing from the gist of the present disclosure also naturally belong to the technical scope of the present disclosure. At least one of various omissions, substitutions, and changes of the components can be made without departing from the gist of the embodiments and the modification described above.

What is claimed is:

1. A detection device comprising:
    a substrate;
    a plurality of photodiodes provided on the substrate;
    a plurality of transistors provided correspondingly to the respective photodiodes;
    a plurality of gate lines that extend in a first direction;
    a plurality of signal lines that extend in a second direction intersecting the first direction;
    a plurality of lower electrodes that are provided between the transistors and the photodiodes in a direction orthogonal to the substrate, and are provided correspondingly to the respective photodiodes;
    an upper electrode provided so as to extend across the photodiodes; and
    a reflective layer provided between the substrate and each of the photodiodes in the direction orthogonal to the substrate, wherein
    each of the lower electrodes has a smaller area than an area defined by the gate lines and the signal lines, and
    the reflective layer is provided between the lower electrodes adjacent to each other in a plan view.

2. The detection device according to claim 1, further comprising:
    an organic insulating film that covers the transistors; and
    an inorganic insulating film provided between the organic insulating film and the lower electrodes, wherein
    the reflective layer is provided between the organic insulating film and the inorganic insulating film.

3. The detection device according to claim 1, wherein
    each of the transistors comprises a semiconductor layer, a gate electrode, and a source electrode, and
    the reflective layer is provided between the substrate and the semiconductor layer in the direction orthogonal to the substrate.

4. The detection device according to claim 1, wherein the reflective layer is provided so as to overlap at least one of the signal lines adjacent to each other in the first direction in the plan view.

5. The detection device according to claim 1, wherein
    each of the transistors comprises a semiconductor layer, a gate electrode, and a source electrode,
    the semiconductor layer, the gate electrode, and the source electrode are stacked in this order in the direction orthogonal to the substrate, and
    the reflective layer is provided in the same layer as that of the source electrode.

6. The detection device according to claim 5, wherein the source electrode is provided so as to overlap the gate electrode.

7. The detection device according to claim 5, wherein the reflective layer is provided so as to overlap at least one of the gate lines adjacent to each other in the second direction in the plan view.

8. The detection device according to claim 1, wherein
    each of the transistors comprises a semiconductor layer, a gate electrode, and a source electrode,
    the semiconductor layer, the gate electrode, and the source electrode are stacked in this order in the direction orthogonal to the substrate, and
    the reflective layer is provided in the same layer as that of the gate electrode.

9. The detection device according to claim 8, wherein the reflective layer provided in the same layer as that of the gate electrode is provided so as to overlap at least one of the signal lines adjacent to each other in the first direction in the plan view.

10. The detection device according to claim 1, wherein
    each of the transistors comprises a semiconductor layer, a bottom gate electrode, and a source electrode,
    the bottom gate electrode, the semiconductor layer, and the source electrode are stacked in this order in the direction orthogonal to the substrate, and
    the reflective layer is provided in the same layer as that of the bottom gate electrode.

11. The detection device according to claim 10, wherein the reflective layer provided in the same layer as that of the bottom gate electrode is provided so as to overlap at least one of the signal lines adjacent to each other in the first direction in the plan view.

* * * * *